(12) United States Patent
Goldan et al.

(10) Patent No.: US 11,841,470 B2
(45) Date of Patent: Dec. 12, 2023

(54) PRISMATOID LIGHT GUIDE

(71) Applicant: The Research Foundation for The State University of New York, Albany, NY (US)

(72) Inventors: Amirhossein Goldan, Stony Brook, NY (US); Andrew Labella, New Rochelle, NY (US); Wei Zhao, East Setauket, NY (US); Anthony Lubinsky, Port Jefferson Station, NY (US)

(73) Assignee: The Research Foundation for The State University of New York, Albany, NY (US)

( * ) Notice: Subject to any disclaimer, the term of this patent is extended or adjusted under 35 U.S.C. 154(b) by 189 days.

(21) Appl. No.: 17/417,552

(22) PCT Filed: Jan. 8, 2020

(86) PCT No.: PCT/US2020/012707
§ 371 (c)(1),
(2) Date: Jun. 23, 2021

(87) PCT Pub. No.: WO2020/146475
PCT Pub. Date: Jul. 16, 2020

(65) Prior Publication Data
US 2022/0120923 A1 Apr. 21, 2022

Related U.S. Application Data

(60) Provisional application No. 62/957,991, filed on Jan. 7, 2020, provisional application No. 62/789,559, filed on Jan. 8, 2019.

(51) Int. Cl.
*G01T 1/29* (2006.01)
*G01T 1/164* (2006.01)
*G01T 1/20* (2006.01)

(52) U.S. Cl.
CPC .......... *G01T 1/2985* (2013.01); *G01T 1/1644* (2013.01); *G01T 1/2002* (2013.01)

(58) Field of Classification Search
CPC ..... A61B 6/037; G01T 1/2985; G01T 1/1644; G01T 1/2002; G01T 1/1642
See application file for complete search history.

(56) References Cited

U.S. PATENT DOCUMENTS

| 3,944,835 A | 3/1976 | Vosburgh |
| 4,394,576 A | 7/1983 | Tananaka et al. |

(Continued)

FOREIGN PATENT DOCUMENTS

| CN | 102597805 | 7/2012 |
| CN | 105655435 | 6/2016 |

(Continued)

OTHER PUBLICATIONS

European Search Report dated Jul. 15, 2022 issued in counterpart Application No. 20738452.0, 8 pages.

(Continued)

*Primary Examiner* — David P Porta
*Assistant Examiner* — Casey Bryant
(74) *Attorney, Agent, or Firm* — The Farrell Law Firm, P.C.; Douglas M. Owens, III

(57) ABSTRACT

Provided area device for detecting sub-atomic particles and method of fabrication thereof. The device includes a plurality of scintillators, a detector provided on a first end of the plurality of scintillators and a prismatoid provided on a second end of the plurality of scintillators. The prismatoid redirects light between adjacent scintillators of the plurality of scintillators.

20 Claims, 13 Drawing Sheets

(56) References Cited

U.S. PATENT DOCUMENTS

| | | | |
|---|---|---|---|
| 4,415,808 A | 11/1983 | Cusano et al. | |
| 5,616,924 A | 4/1997 | Petrillo | |
| 6,288,399 B1 | 9/2001 | Andreaco et al. | |
| 6,516,044 B1* | 2/2003 | Lyons | A61B 6/00 250/336.1 |
| 7,088,901 B2 | 8/2006 | Kim et al. | |
| 7,132,664 B1 | 11/2006 | Crosetto | |
| 7,601,963 B2 | 10/2009 | Aykac et al. | |
| 8,350,218 B2 | 1/2013 | Thon et al. | |
| 8,436,312 B2 | 5/2013 | Inadama et al. | |
| 9,304,211 B2* | 4/2016 | Goertzen | G01T 5/08 |
| 9,599,724 B2 | 3/2017 | Wieczorek et al. | |
| 9,618,631 B2 | 4/2017 | Zerrouk et al. | |
| 9,645,258 B1 | 5/2017 | Reyna | |
| 9,696,439 B2* | 7/2017 | An | H01L 27/14663 |
| 9,720,102 B1 | 8/2017 | Page et al. | |
| 9,915,739 B2 | 3/2018 | Benlloch Baviera et al. | |
| 10,024,999 B1 | 7/2018 | Kasten et al. | |
| 10,527,738 B2 | 1/2020 | Weedon et al. | |
| 11,454,730 B2* | 9/2022 | Goldan | A61B 6/4208 |
| 2005/0087692 A1 | 4/2005 | Romanov et al. | |
| 2008/0121806 A1 | 5/2008 | Grazioso | |
| 2010/0270463 A1 | 10/2010 | Lee et al. | |
| 2011/0017916 A1 | 1/2011 | Schulz et al. | |
| 2011/0121184 A1 | 5/2011 | Inadama et al. | |
| 2011/0192981 A1 | 8/2011 | Menge et al. | |
| 2011/0192982 A1 | 8/2011 | Henseler et al. | |
| 2012/0061577 A1* | 3/2012 | Oleinik | G01T 1/2002 250/366 |
| 2012/0235047 A1 | 9/2012 | Lewellen et al. | |
| 2013/0112856 A1 | 5/2013 | Ferenc | |
| 2014/0064446 A1 | 3/2014 | Wear et al. | |
| 2014/0299777 A1* | 10/2014 | Oleinik | G01T 1/2018 250/366 |
| 2014/0353510 A1 | 12/2014 | Spanoudaki et al. | |
| 2015/0355346 A1 | 12/2015 | Weston et al. | |
| 2016/0223688 A1 | 8/2016 | Yamashita et al. | |
| 2016/0223690 A1* | 8/2016 | Uchida | G01T 1/1644 |
| 2016/0231439 A1 | 8/2016 | Trost et al. | |
| 2017/0123084 A1 | 5/2017 | Ferenc | |
| 2017/0234990 A1 | 8/2017 | Sowards-Emmerd et al. | |
| 2017/0285182 A1* | 10/2017 | Fu | G01T 1/2985 |
| 2019/0053772 A1 | 2/2019 | Benlloch Baviera et al. | |
| 2019/0223725 A1 | 7/2019 | Lu et al. | |
| 2020/0326434 A1* | 10/2020 | Goldan | A61B 6/4225 |

FOREIGN PATENT DOCUMENTS

| | | |
|---|---|---|
| CN | 107076859 | 8/2017 |
| CN | 206725802 | 12/2017 |
| CN | 111971585 | 11/2020 |
| CN | 113614574 | 11/2021 |
| DE | 2912210 | 10/1979 |
| DE | 69929027 | 8/2006 |
| EP | 0437051 | 5/1995 |
| EP | 3054319 | 8/2016 |
| EP | 3532876 | 9/2019 |
| EP | 3908856 | 8/2022 |
| ES | 2 727 282 | 10/2019 |
| JP | H 05203755 | 8/1993 |
| JP | H 085746 | 1/1996 |
| JP | H 0961533 | 3/1997 |
| JP | H 09325185 | 12/1997 |
| JP | H 10232284 | 9/1998 |
| JP | 2955487 | 10/1999 |
| JP | 2000193749 | 7/2000 |
| JP | 2000258540 | 9/2000 |
| JP | 2003265457 | 9/2003 |
| JP | 2005099027 | 4/2005 |
| JP | 5110879 | 12/2012 |
| JP | 5405866 | 2/2014 |
| JP | 2014527690 | 10/2014 |
| JP | 2016142561 | 8/2016 |
| JP | 2016537640 | 12/2016 |
| JP | 2019163970 | 9/2019 |
| JP | 6862427 | 4/2021 |
| JP | 7183140 | 12/2022 |
| KR | 10-2009-0057831 | 6/2009 |
| KR | 1020130095613 | 8/2013 |
| KR | 10-2015-0095115 | 8/2015 |
| KR | 1020190056975 | 5/2019 |
| KR | 1020190058193 | 5/2019 |
| WO | WO 2009033038 | 3/2009 |
| WO | WO 2012093526 | 7/2012 |
| WO | WO 2014194028 | 12/2014 |
| WO | WO 2016/112135 | 7/2016 |
| WO | WO 2018/119070 | 6/2018 |
| WO | WO 2019098629 | 5/2019 |
| WO | WO 2019177461 | 9/2019 |
| WO | WO 2020013689 | 1/2020 |
| WO | WO 2020146475 | 7/2020 |
| YU | 562/03 | 8/2006 |

OTHER PUBLICATIONS

M. Pizzichemi et al., "A new method for depth of interaction determination in PET detectors", 2016 Phys. Med. Biol. 61 4679, pp. 21.

H. Uchida et al., "A novel single-ended readout depth of interaction PET detector fabricated using sub-surface laser engraving", 2016 Phys. Med. Biol. 61 6635, pp. 17.

G. Stringhini et al., "Development and evaluation of a practical method to measure the Depth of Interaction function for a single side readout PET detector", . . . 2016 JINST 11 P11014, pp. 15.

Y. Shao et al., "Development of a prototype PET scanner with depth-of-interaction measurement using solid-state photomultiplier arrays and parallel readout electronics" . . . 2014 Phys. Med. Biol. 59 1223, pp. 17.

N. Inadama et al., "DOI PET Detectors with Scintillation Crystals Cut as Triangular Prisms", 2008 IEEE Nuclear Science Symposium Conference Record, © 2008 IEEE, pp. 3942-3945.

S. Cuddy et al., "Effect of scintillator crystal geometry and surface finishing on depth of interaction resolution in PET detectors: Monte Carlo simulation and experimental . . . Results using silicon photomultipliers", Proc. SPIE 7622, Medical Imaging 2010: Physics of Medical Imaging, 76221O (Mar. 22, 2010), pp. 9.

E. Berg, PhD et al., "Innovations in Instrumentation for Positron Emission Tomography", © 2018 Elsevier Inc., pp. 311-331.

L. Bläckberg et al., "Light Spread Manipulation in Scintillators Using Laser Induced Optical Barriers", IEEE Transactions on Nuclear Science, . . . vol. 65, No. 8, Aug. 2018, pp. 8.

L. Bläckberg et al., "Simulation study of light transport in laser-processed LYSO: Ce detectors with single-side readout", 2017 Phys. Med. Biol. 62 8419, pp. 23.

J. Kang et al., "Simulation study of PET detector configuration with thick light guide and GAPD array having large-area microcells for high effective quantum efficiency" . . . Computer Methods and Programs in Biomedicine 131 (2016) 79-87, © 2016 Elsevier Ireland Ltd., pp. 9.

PCT/ISA/237 Written Opinion issued on PCT/US2020/012707, dated May 6, 2020, pp. 3.

PCT/ISA/210 Search Report issued on PCT/US2020/012707, dated May 6, 2020, pp. 7.

Makek, Mihael et al., "Scintillator Pixel Detectors for Measurement of Compton Scattering", Condensed Matter, Feb. 15, 2019, pp. 13.

Schmitz, Ruth E. et al., "The Physics of PET/CT scanners", Physics, 2013, pp. 16.

Marcinkowski, R. et al., "Optimized light sharing for high-resolution Tof Pet detector based on digital silicon photomultipliers", Phys. Med. Biol. 59 (2014) 7125-7139.

Song, Tae Yong et al., "A sub-millimeter resolution PET detector module using a multi-pixel photon counter array", Phys. Med. Biol. 55 (2010) 2573-2587.

* cited by examiner

PRISMATOID LIGHT GUIDE

PRIORITY

This application claims priority to U.S. Provisional Patent Applications No. 62/789,559 and 62/957,991 filed with the U.S. Patent and Trademark Office on Jan. 8, 2019 and Jan. 7, 2020, respectively, the entire contents of each which is incorporated herein by reference.

GOVERNMENT SUPPORT

This invention was made with government support under grant number EB024849 awarded by the National Institutes of Health. The government has certain rights in the invention.

BACKGROUND OF THE INVENTION

1. Field of the Invention

The present invention relates generally to the field of radiation imaging and, in particular, to positron emission tomography (PET).

2. Description of the Related Art

PET is a nuclear medical imaging modality that produces three-dimensional (3D) images to see functional processes in a living organism. PET is commonly used in clinical oncology for detecting cancer and for clinical diagnosis of heart problems and/or brain disorders. After being introduced into the organism, positron-emitting radionuclides decay with each annihilation, emitting two photons in diametrically opposing directions. Time of flight (TOF) measurements may be utilized to measure the time for the electromagnetic wave to travel a distance through a medium. A TOF PET system detects the photons, and uses TOF information to determine if two registered photons are in time coincidence, i.e., belong to a same positron annihilation event. The TOF PET system uses an arrival time difference to localize each annihilation event. Without the TOF localization data, computationally expensive iterative reconstruction algorithms are used to estimate the 3D distribution of events that provide the best match with the measured projection data. Modern PET readout is performed with silicon photomultipliers (SiPMs) due to their speed and magnetic resonance compatibility.

High depth-of-interaction (DOI) resolution is needed in PET scintillators to reduce parallax error and the resulting spatial blur, which is especially prominent in detection system with small ring diameters, such as single-organ inserts. DOI readout is traditionally performed with a double-sided readout using two readout arrays per scintillator array. However, the double-sided readout requires double electronics compared to a regular PET system. Therefore, recent research has focused on the development of single-sided readout techniques, which only requires one scintillator and one readout array. Multiple scintillator crystals are typically coupled to single readout pixels to reduce system cost, although 1:1 coupling can also be used.

Modern DOI techniques use substantially flat reflective light guides at the top of the scintillator array to redirect light to other readout pixels. In doing so, DOI information can be gained by detection of a fraction of the maximum light absorbed on a single SiPM pixel and the detected fraction to the total light absorbed across all pixels of an array for a single gamma ray interaction event. Only two different readout pixels are required to make this measurement. However, having more pixels is useful to improve the DOI resolution.

Conventional light guide geometry uses a flat, uniform reflective material, which primarily directs light back into the original scintillation crystal that gamma ray absorption took place in, rather than redirecting the light to other crystals and readout pixels. This results in suboptimal DOI resolution since most of the light is not being shared with other pixels, which is required to make DOI measurements, thus making single-sided DOI readout ineffective. Current single-sided DOI readout with high aspect ratio scintillators (~15-20 mm thick) and uniform light guides are only able to achieve ~5 mm full width at half maximum (FWHM) DOI resolution. In contrast, double-sided readout can achieve DOI resolution on the order of 1 mm FWHM, leaving much room for improvement of single-sided techniques before they become feasible to use in practice. Conventional systems and methods fail to provide impactful light sharing techniques in PET detector systems.

Anger logic schemes are traditionally employed to improve the overall detector system resolution by localizing gamma ray interaction down to the crystal level via centroiding. Because of poor light sharing of conventional uniform light guides, Anger logic localization on the periphery of the detector array is severely degraded compared to that of centralized crystals and detectors since peripheral crystals have fewer crystals and pixels for sharing.

SUMMARY OF THE INVENTION

To overcome shortcomings of conventional systems, provided herein are a system and method for improved light sharing between scintillator crystals in PET detector systems. The present disclosure overcomes the shortcomings of conventional DOI readout systems and methods, provides improved DOI resolution and more uniform Anger logic localization performance across entire detector arrays.

Accordingly, aspects of the present invention address the above problems and disadvantages and provide the advantages described below. An aspect of the present invention provides a device for detecting sub-atomic particles, the device including a plurality of scintillators, at least one detector provided on a first end of the scintillator, and a prismatoid provided on a second end of the scintillator, with the prismatoid configured to redirect light between a first pair of adjacent scintillators of the plurality of scintillators.

An aspect of the present disclosure provides a prismatoid that includes a reflective surface configured to redirect travel of at least one photon emitted from at least one scintillator of a pair of scintillators adjacent to the reflective surface, with the travel of the at least one photon being redirected from the at least one scintillator of a first pair of scintillators toward another scintillator of the first pair of scintillators.

A further aspect of the present disclosure provides a system for non-invasive medical imaging that includes at least one prismatoid, at least one detector, and a scintillator array. The at least one prismatoid redirects light between adjacent scintillators of scintillator array. The at least one detector is provided on an end of the scintillator array opposite the at least one prismatoid, and the prismatoid is substantially shaped as at least one of at least one prism, at least one antiprism, at least one frustum, at least one triangle, at least one cupola, at least one parallelepiped, at least one wedge, at least one pyramid, at least one truncated pyramid, and at least one portion of a sphere.

BRIEF DESCRIPTION OF THE DRAWINGS

The above and other aspects, features and advantages of certain embodiments of the present invention will be more apparent from the following detailed description taken in conjunction with the accompanying drawings, in which.

DETAILED DESCRIPTION OF EMBODIMENTS OF THE INVENTION

The following detailed description of certain embodiments of the present invention will be made with reference to the accompanying drawings. In describing the invention, explanation about related functions or constructions known in the art are omitted for the sake of clarity, to avoid obscuring the invention with unnecessary detail.

Figure 1:
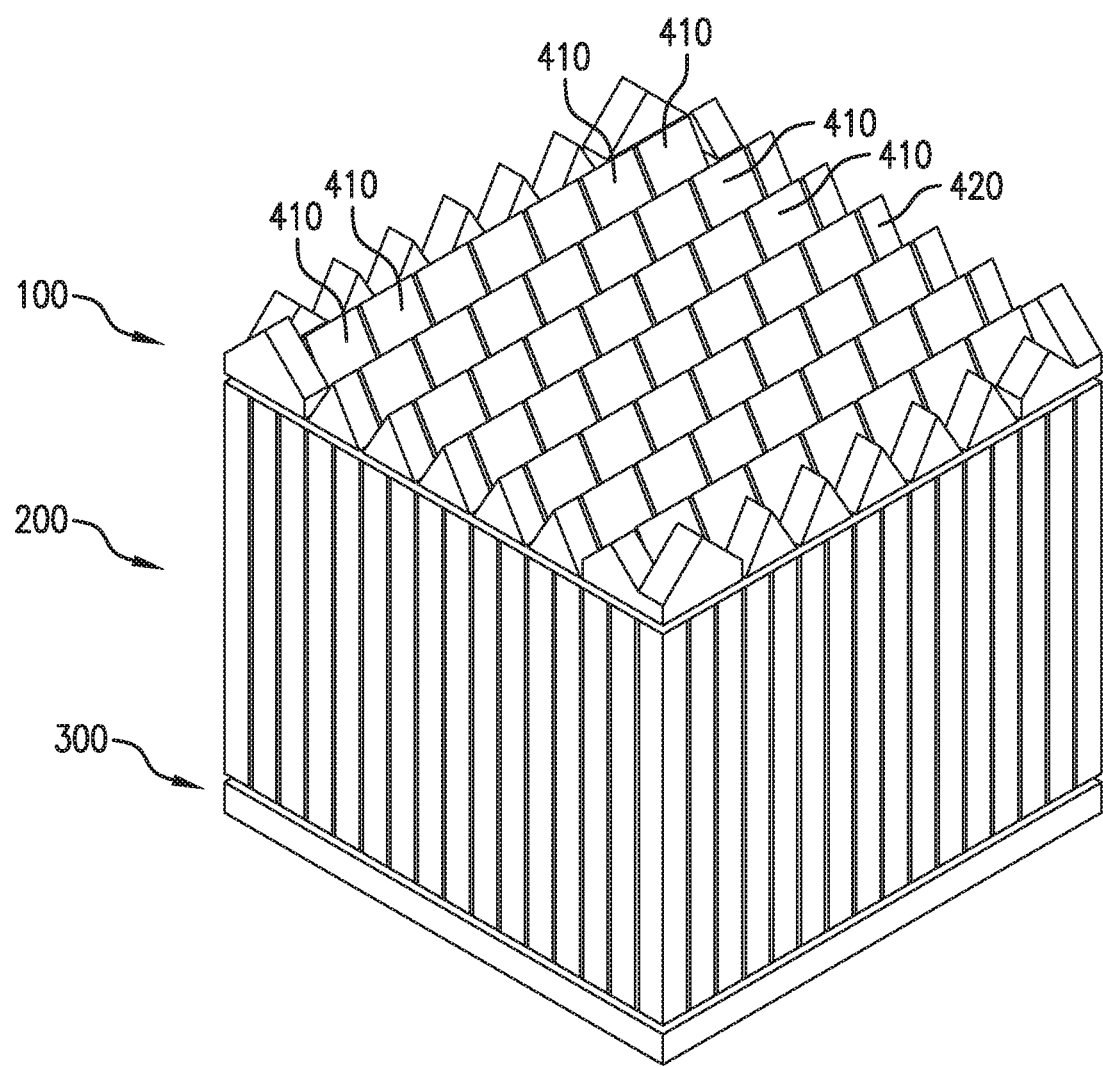
FIG. 1 is a perspective view of the prismatoid light guide, according to an embodiment of the present disclosure.

FIG. 1 is a perspective view of the prismatoid light guide, according to an embodiment of the present disclosure. The prismatoid light guide 100 of FIG. 1 is positioned on the scintillator array 200, with a detector 300 positioned on a side opposite the prismatoid light guide 100. As illustrated in FIG. 1, the prismatoid light guide 100 includes a plurality of first prismatoids 410, which may be triangular shaped, and which may be surrounded by second prismatoids 420 and corner prismatoids, details of which are provided herein. The prism light guide 100 may be fixedly provided or removably provided on the scintillator array 120.

Figure 2:
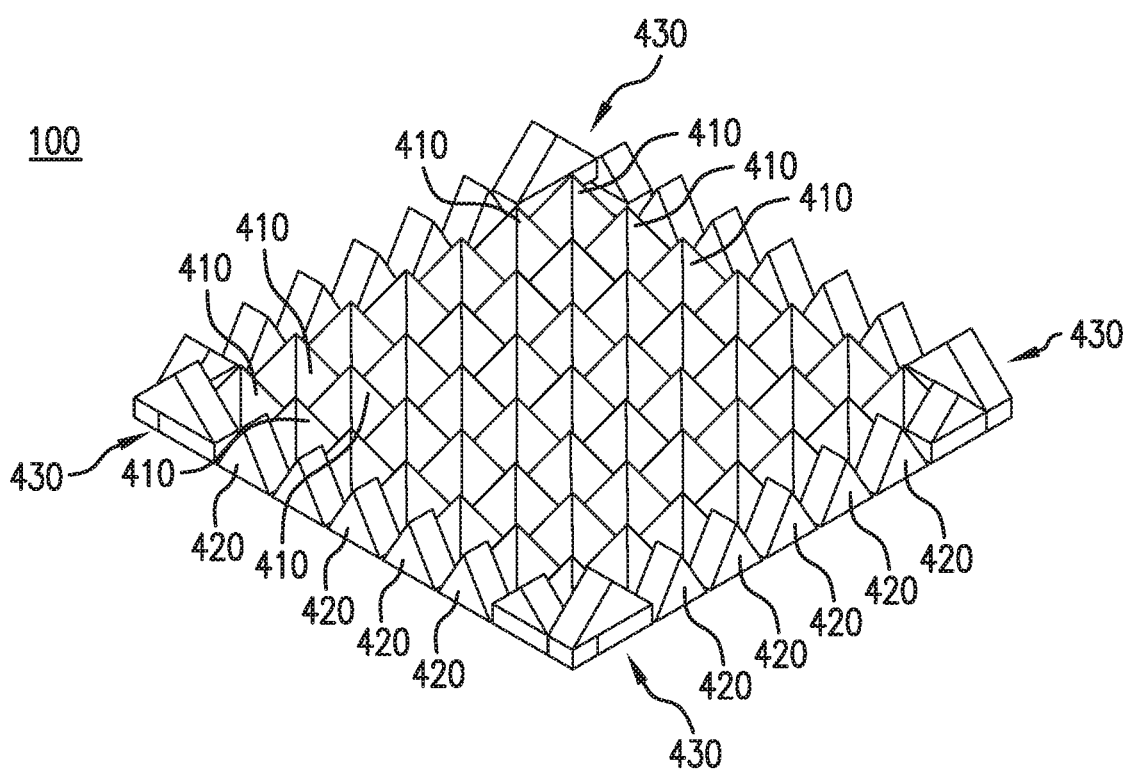
FIG. 2 is a perspective view of a prismatoid light guide, according to an embodiment of the present disclosure.

FIG. 2 is a perspective view of the prismatoid light guide 100. As illustrated in FIG. 2, the plurality of first prismatoids 410 may be substantially pyramid shaped. The first prismatoids 410, the second prismatoids 420 and the third prismatoids may be substantially shaped as at least one of at least one prism, at least one antiprism, at least one frustum, at least one triangle, at least one cupola, at least one parallelepiped, at least one wedge, at least one pyramid, at least one a truncated pyramid, and at least one a portion of a sphere.

Figure 3:
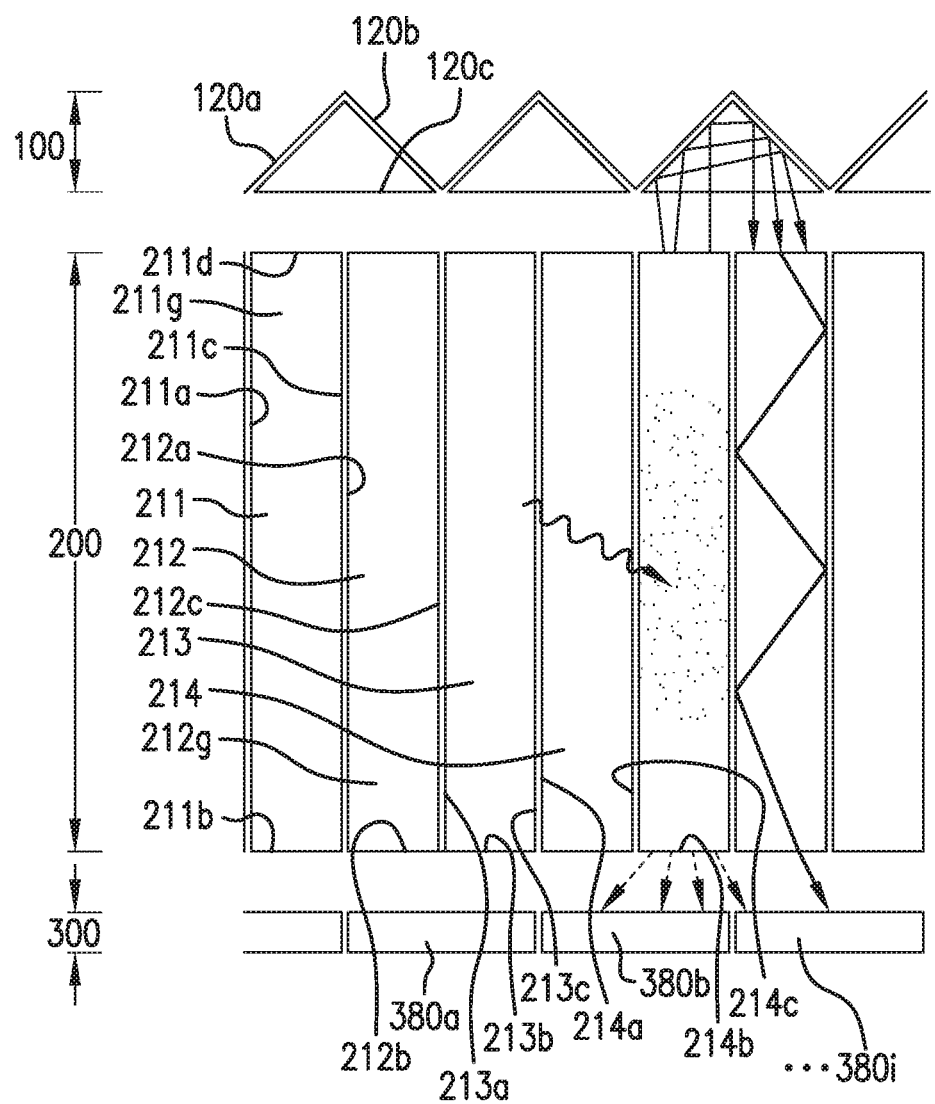
FIG. 3 is a cut away profile view of a prismatoid light guide positioned on a scintillator array, according to an embodiment of the present disclosure.

FIG. 3 is a cut away profile view illustrating a geometric arrangement of a center portion of the prismatoid light guide 100 positioned on a scintillator array 200, according to an embodiment of the present disclosure. As illustrated in FIG. 3, the prismatoid may be substantially shaped as a pyramid with three sides 120a, 120b, 120c. The prismatoid light guide 100 may be positioned on or adjacent to a first end 211d, i.e., a first end face, of the scintillator array 200. The prismatoid light guide 100 operates as a reflector that enhances light sharing and provides at least 4:1 coupling between scintillators 211, 212, 213, 214. The prismatoid light guide 100 includes at least one reflective surface, e.g., an interior surface of sides 120a, 120b, that redirects travel of at least one sub-atomic particle, e.g., a photon, emitted from at least one scintillator of a first pair of adjacent scintillators. The interior surface of sides 120a, 120b may be coated with Barium Sulfate, epoxy or provided with an enhanced specular reflector (ESR) insert for improved reflectivity along lateral face thereof. Each scintillator of the scintillator pair of scintillators may be a scintillator crystal, configured to convert high energy x-rays, gamma rays and similar high energy particles into optical light and/or photons, as known in the art. The change of travel direction is from the at least one scintillator that emits the at least one sub-atomic particle towards at least one other scintillator of the at least four adjacent scintillators. The provided coupling enhances detection by silicon photomultipliers (SiPM) pixels 380a, 380b, 380c . . . 380i of detector 300, positioned at a second end 211b. The SiPM pixels 380a . . . 380i of detector 300 communicate with at least one processor, which controls a display or other output of the at least one photon that is detected by the detector 300, to provide a single-sided readout high resolution of depth-of-interaction (DOI) readout in a positron emission tomography (PET) detector.

Each scintillator 211, 212, 213, 214 may include a first interior side 211a, 212a and a second interior side 211c, 212c. The second interior side 211c, 212c may be substantially parallel with the respective first interior side 211a, 212a, and the first interior side 211a, 212a and the second interior side 211c, 212c run substantially from the first end 211d to the second end 211b, thereby providing an interior light guide 211g, 212g between each respective first side 211a, 212a and second side 211c, 212c configured to reflect light therebetween, for transmitting substantially all of the light from respective prismatoids 120 of the prism light guide 100 to respective detectors 300. The interior light guide reflects substantially all light within respective scintillators 211, 212, 213, 214 traveling from respective prismatoids 120 to respective detectors 130. As illustrated in FIG. 9B, the prismatoid 120 redirects light from the light guide of a first scintillator to the light guide of adjacent scintillators, and light sharing is self-contained within scintillation crystals coupled to the prismatoid 120.

The prismatoid 120 provides stabilized light guide geometry at the first end face 211d of the scintillator array 100. The prismatoid light guide 100 reflects light, without functioning as a high-energy photon detector. As illustrated in FIGS. 3, 4, 8a and 8b, the scintillators 211, 212, 213, 214 may be coupled in a 4:1 ratio for photon detection by a shared SiPM pixel, e.g., SiPM pixel 380a and SiPM pixel 380b being shared by scintillators 211, 212, 213, 214 via prismatoid 120 of prismatoid light guide 100.

At least two SiPM pixels 380a, 380b of the detector 300 are coupled to a respective prismatoid 120 via scintillator crystals 211, 212, 213, 214, to enable differential single-sided readout for DOI capabilities. FIGS. 3, 4, 8a and 8b illustrate a 1:4 scintillator-to-readout coupling ratio. Prismatoid 120 may be coupled to one end of crystals 211, 212, 213, 214, and SiPM pixels 380a, 380b may be coupled to an opposite end. Other coupling ratios can also be used with varied prismatoid geometry, with the prismatoid 120 being substantially shaped as at least one of at least one prism, at least one antiprism, at least one frustum, at least one triangle, at least one cupola, at least one parallelepiped, at least one wedge, at least one pyramid, at least one a truncated pyramid, and at least one a portion of a sphere.

Figure 4:
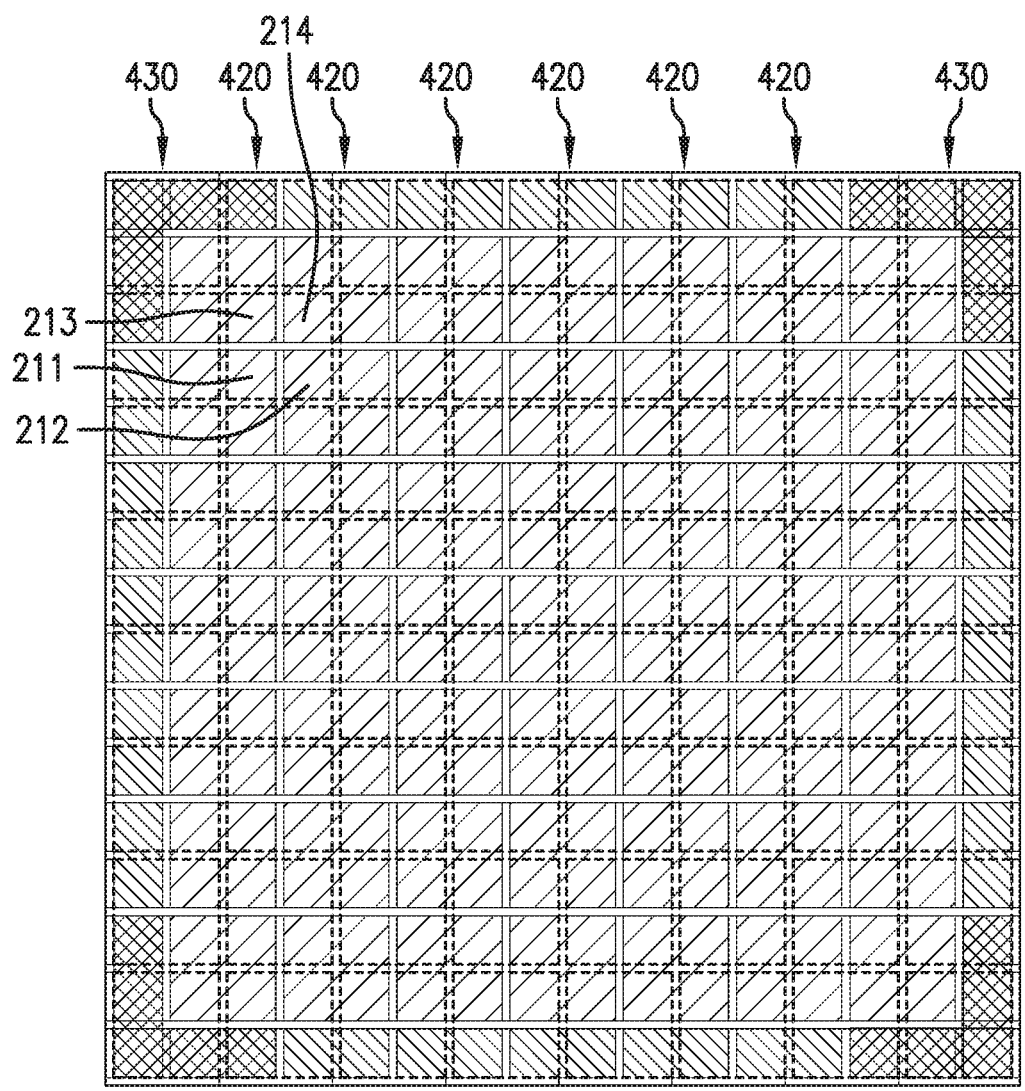
FIG. 4 is a top view of a prismatoid light guide, according to an embodiment of the present disclosure.

FIG. 4 is a top view of the prismatoid light guide 100, with locations of varied prismatoid geometries to introduce more uniformly directed light sharing along edges of the scintillator array 200. The geometry of the prismatoid array allows for coupling of each non-peripheral prismatoid to four SiPM pixels of detector 300 and improved controlled light sharing. FIG. 4 illustrates scintillators 211, 212, 213, 214 sharing a common detector 300. Scintillators 211 and 212 may also be provided as a first pair of adjacent scintillators, and scintillators 213, 214 may be provided as a second pair of adjacent scintillators, with the first scintillator of the first pair of adjacent scintillators adjacent to a first scintillator of the second pair of adjacent scintillators, and the first scintillator of the first pair of adjacent scintillators sharing a first detector of a plurality of detectors with the first scintillator of the second pair of adjacent scintillators. The second scintillator of the first pair of adjacent scintillators may be adjacent to a second scintillator of the second pair of adjacent scintillators, and the second scintillator of the first pair of adjacent scintillators may share a second detector of the plurality of detectors with the second scintillator of the second pair of adjacent scintillators. Accordingly, the prismatoid may redirect light from the first scintillator of the first pair of adjacent scintillators to at least one of the second scintillator of the first pair of adjacent scintillators, the first scintillator of the second pair of adjacent scintillators, and the second scintillator of the second pair of adjacent scintillators.

The controlled light sharing of the present disclosure increases system-level count rate. In contrast, in a uniform light guide, each scintillation event requires readout from all SiPM pixels to calculate the DOI and perform centroiding, since light is expected to be shared across all scintillators. On the other hand, the prismatoid light guide of the present disclosure provides precise identification of which scintillator columns will share light with each other. Scintillators will only share light with columns coupled to a same prismatoid. As illustrated, each non-peripheral prismatoid is coupled to at least four scintillators, which belong to anywhere from at least two to four SiPM pixels depending on the detector array geometry. As a result, readout is only required for a smaller subset of pixels at a time for each scintillation event, enabling simultaneous readout in other parts of the detector array, thereby increasing the system-level count rate when compared with the count rate of a detector system using a conventional uniform light guide.

Figure 5A:
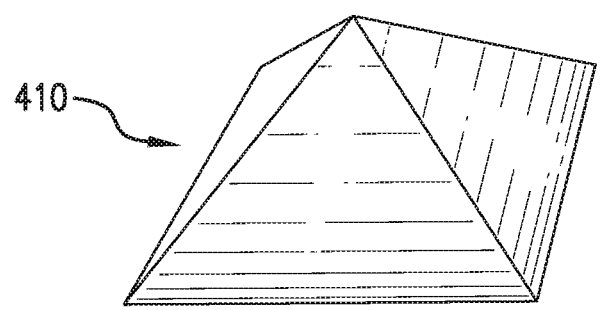
FIGS. 5a-5c are perspective views of prismatoids, according to embodiments of the present disclosure.
Figure 5B:
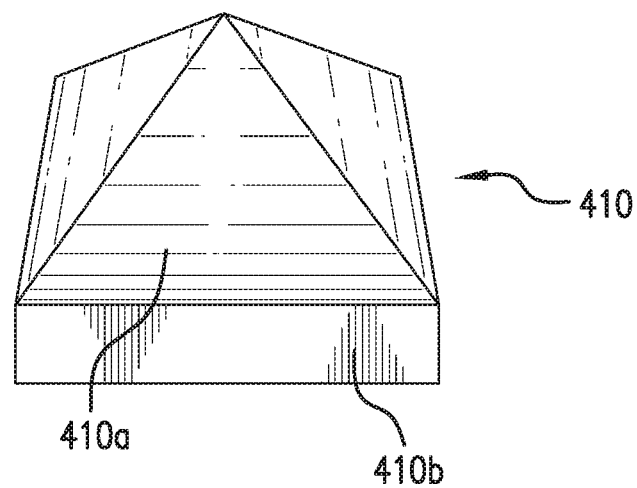
Figure 5C:
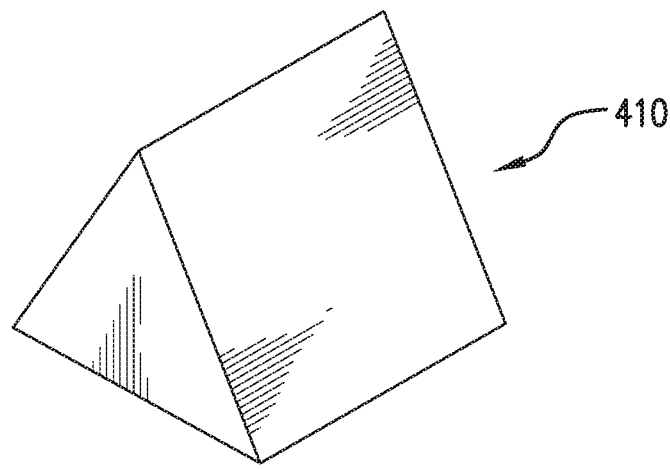

FIGS. 5a-5c are perspective views of prismatoids, according to embodiments of the present disclosure. FIG. 5a is a perspective view of a first prismatoid 410 in a substantially pyramid shape. FIG. 5b is a perspective view of a first prismatoid 410 in shape that combines a substantially pyramid shape with a substantially cuboid shape. FIG. 5c is a perspective view of a first prismatoid 410 in a substantially triangular shape.

Figure 6:
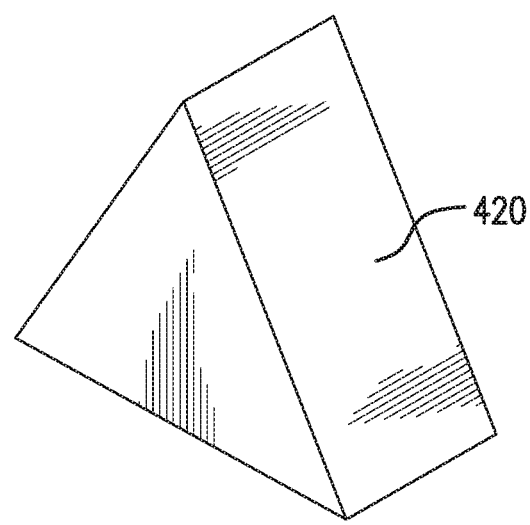
FIG. 6 is a perspective view of a second prismatoid, according to an embodiment of the present disclosure.

FIG. 6 is a perspective view of a second prismatoid 420. The second prismatoid 420 has a substantially triangular shape.

Figure 7A:
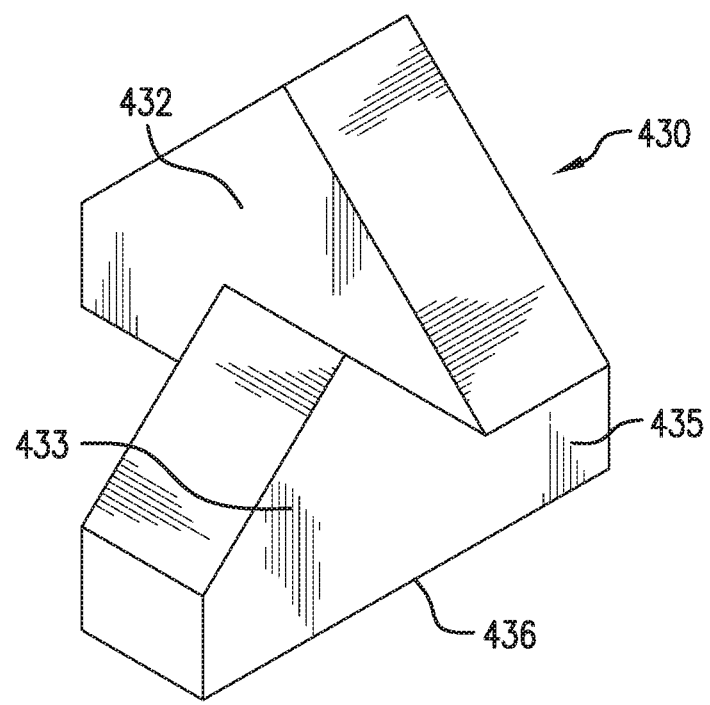
FIGS. 7a and 7b are perspective views of prismatoids, according to embodiments of the present disclosure.
Figure 7B:
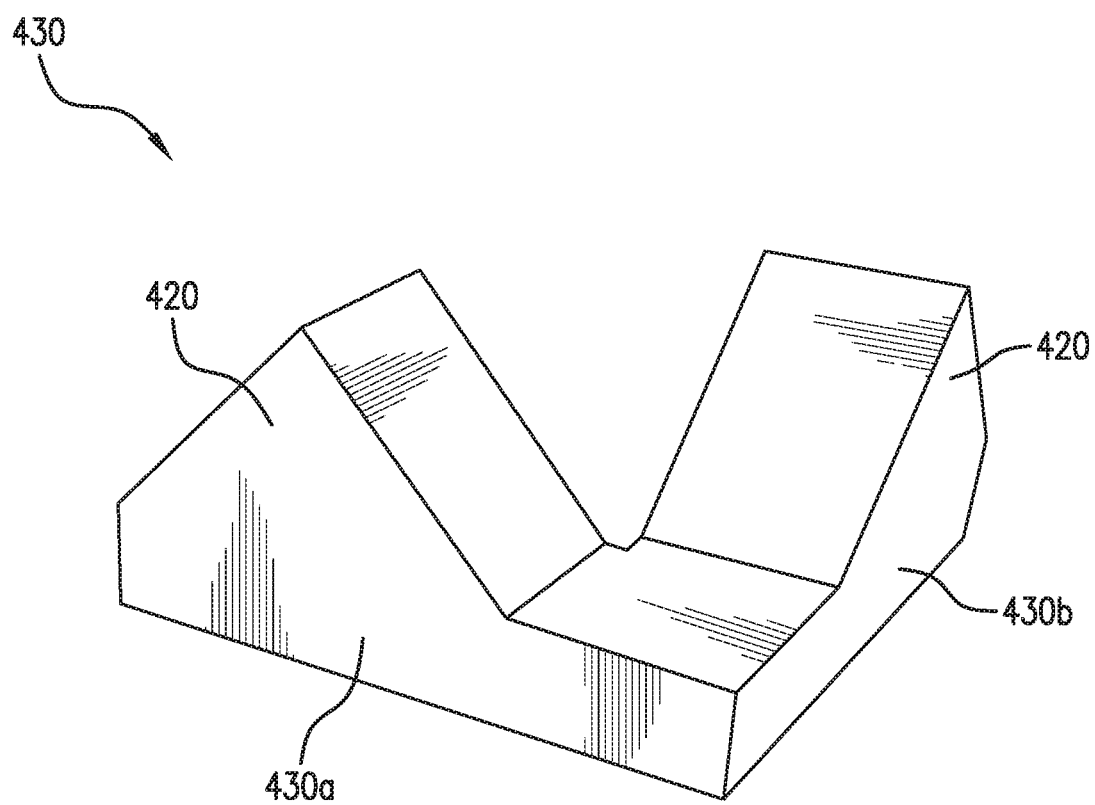

FIGS. 7a and 7b are perspective views of prismatoids 430. FIG. 7a illustrates a corner prismatoid that includes substantially cuboid shapes 435, 436, upon which substantially triangular shapes 432, 433 are respectively affixed. The cuboid shapes 435, 436 may also be monolithically formed on triangular shapes 432, 433. FIG. 7b illustrates a corner prismatoid that includes substantially cuboid shapes 430a, 430b, upon which substantially triangular shapes 430c, 430d are respectively affixed. Arrangement of the first prismatoid 410, the third prismatoid 420 and the third prismatoid 430 is provided in FIGS. 2-4.

Increased uniformity of Anger logic centroiding resolution throughout the detector array is provided, since light is purposely directed to other pixels. In contrast, in conventional uniform light guides do not specifically couple or purposely direct light to specific other SiPM pixels. Also, conventional uniform light guides introduce edge effects where centroiding resolution decreases drastically along the edges of the scintillator array. In contrast, the configuration of the first prismatoid 410, the second prismatoid 420 and the third prismatoid 430 is completely symmetrical regarding light sharing between scintillators and eliminates edge effects in conventional systems. See, FIGS. 2-4.

Figure 8A:
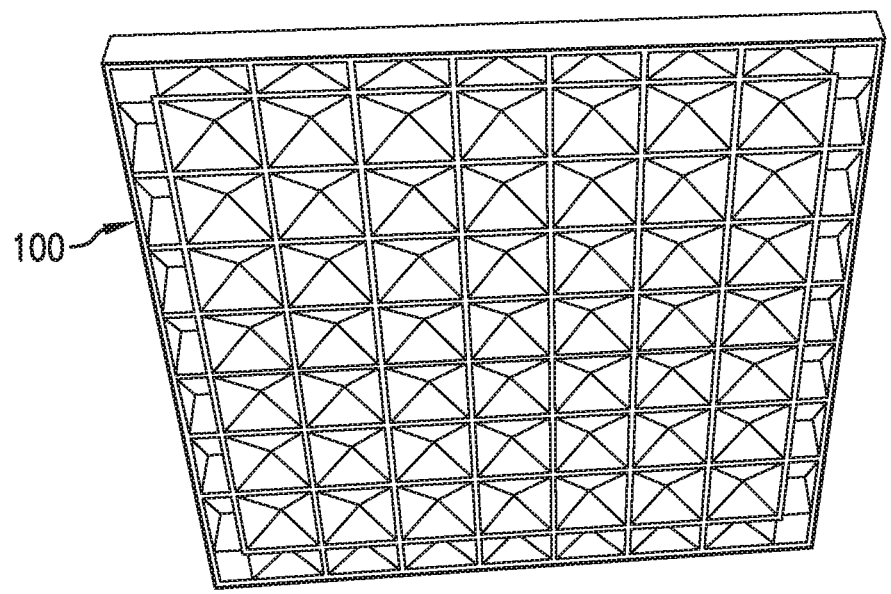
FIG. 8a illustrates a prismatoid light guide array disassembled from a scintillator array, according to an embodiment of the present disclosure.
Figure 8B:
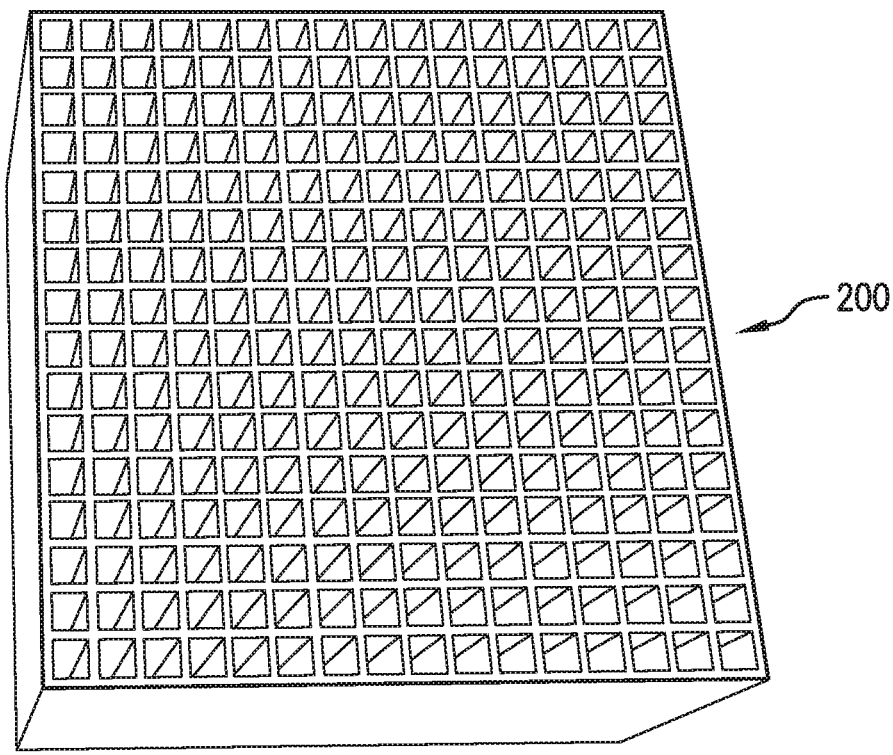
FIG. 8b illustrates a scintillator array disassembled from a prismatoid light guide array, according to an embodiment of the present disclosure.

FIG. 8a illustrates a prismatoid light guide array disassembled from a scintillator array, according to an embodiment of the present disclosure. FIG. 8b illustrates a scintillator array disassembled from a prismatoid light guide array, according to an embodiment of the present disclosure. Assembly of the prismatoid light guide array 100 of FIG. 8a onto the scintillator array 200 of FIG. 8b provides a 4:1 scintillator to prismatoid ratio. The prismatoid light guide array 100 and the scintillator array 200 may also be monolithically provided.

Figure 9A:
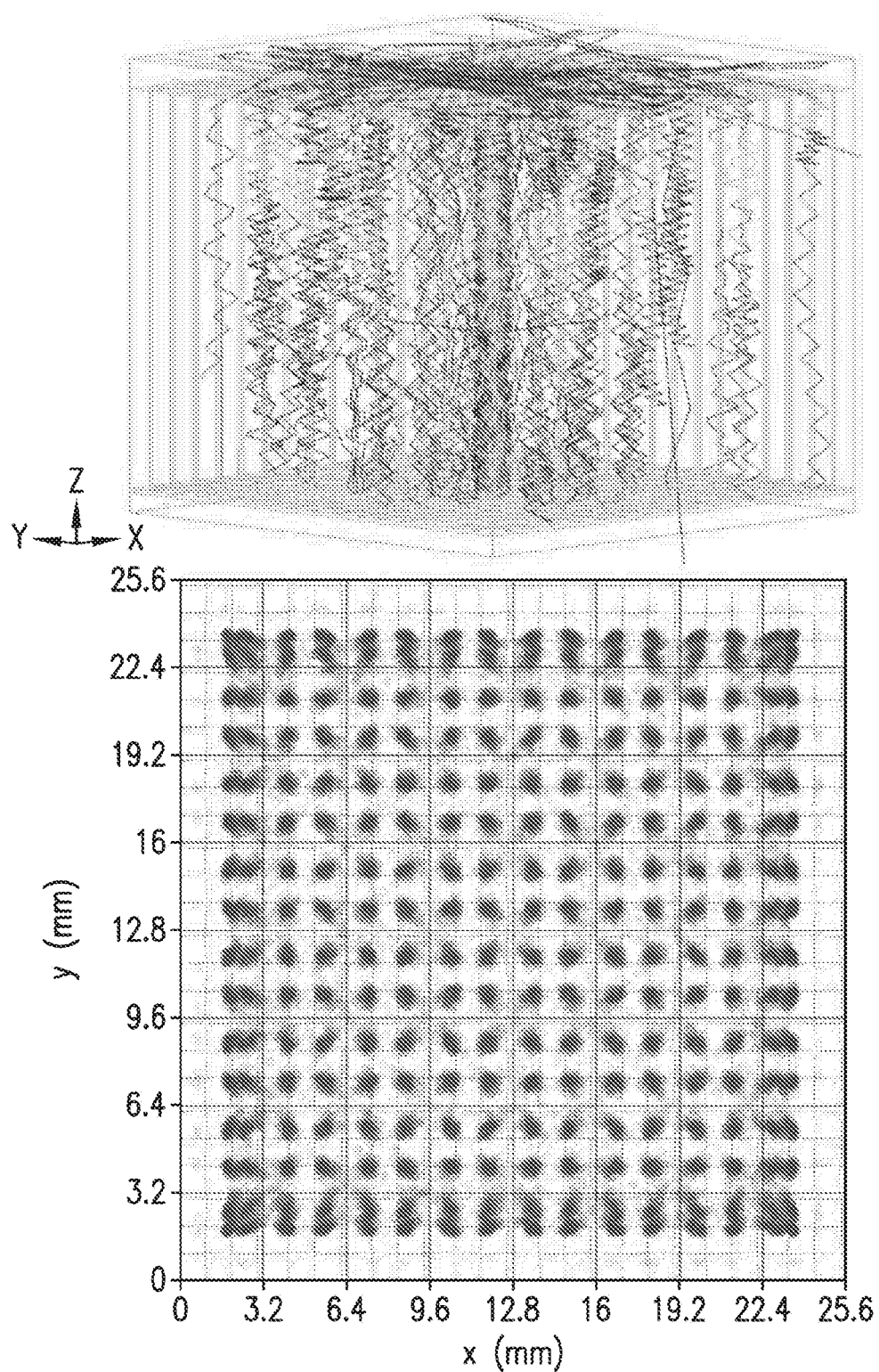
FIG. 9(a) illustrates light sharing of a conventional planar light guide.
Figure 9B:
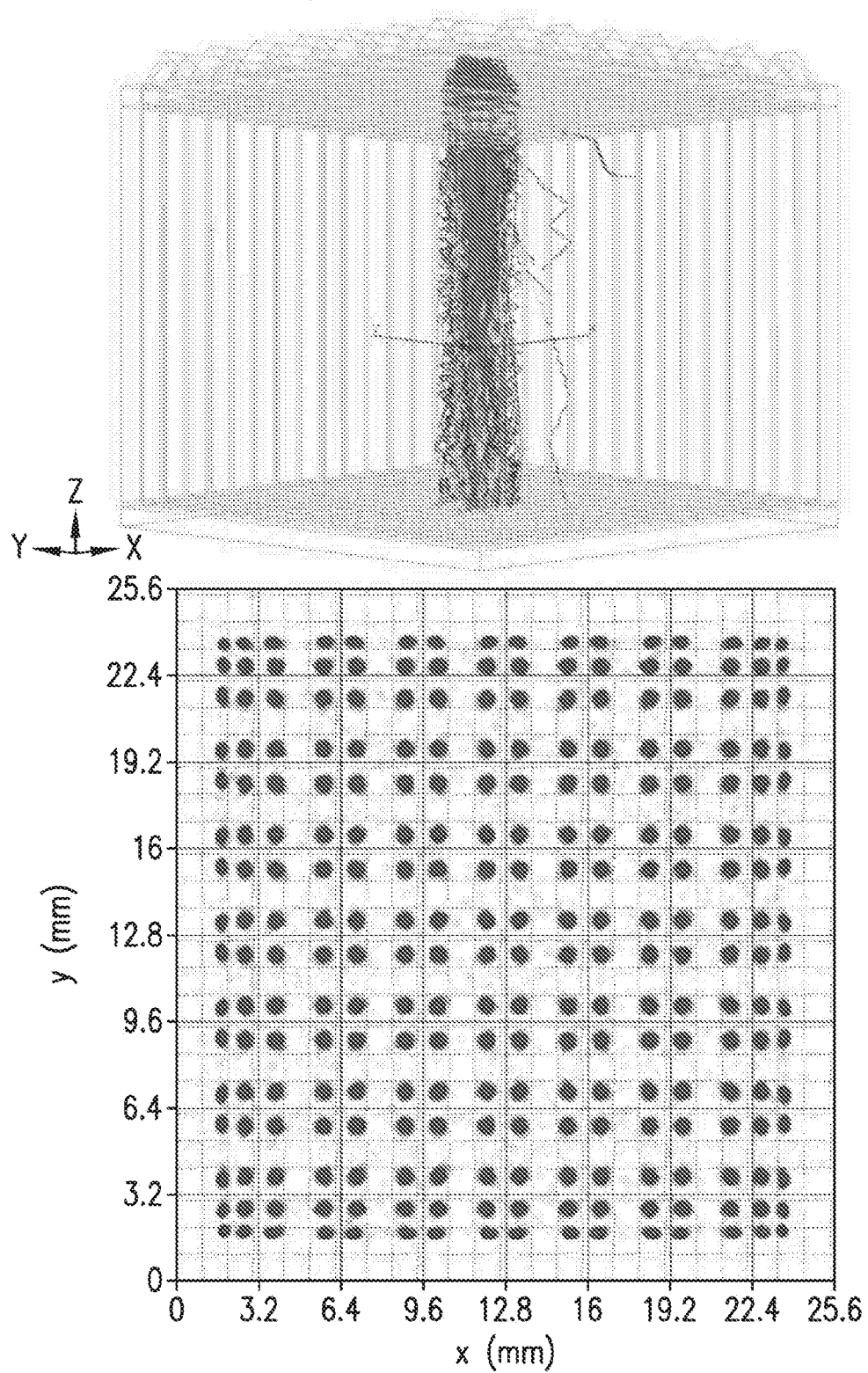
FIG. 9(b) illustrates light sharing of a prismatoid, according to an embodiment of the present disclosure.

FIG. 9(a) illustrates light sharing of a conventional planar light guide. FIG. 9(b) illustrates light sharing of a prismatoid light guide according to an embodiment of the present disclosure. FIGS. 9(a) and 9(b) are obtained by Monte Carlo simulation. FIGS. 9A and 9B provide flood histograms at the upper portion thereof and one dimensional histograms of gamma ray interaction localization in the x-direction representative of crystal identification quality at the lower portion thereof. FIG. 9A illustrates non-uniform scintillator column identification with the uniform glass light guide using Anger logic centroiding due to edge and corner effects. FIG. 9b illustrates elimination of edge and corner effects due to improved light sharing patterns, thereby enabling uniform scintillator column identification throughout the detector array in accordance with an aspect of the present disclosure.

Comparison of the ray traces of FIG. 9(a) with the ray traces of FIG. 9(b) show improved sharing of light with neighboring scintillator column provided by prismatoid light guide 100. As shown in FIG. 9(b), the prismatoid redirects light into neighboring scintillators and SiPM pixels, thus enabling more accurate DOI readout due to enhanced light sharing between neighboring scintillators.

Figure 10:
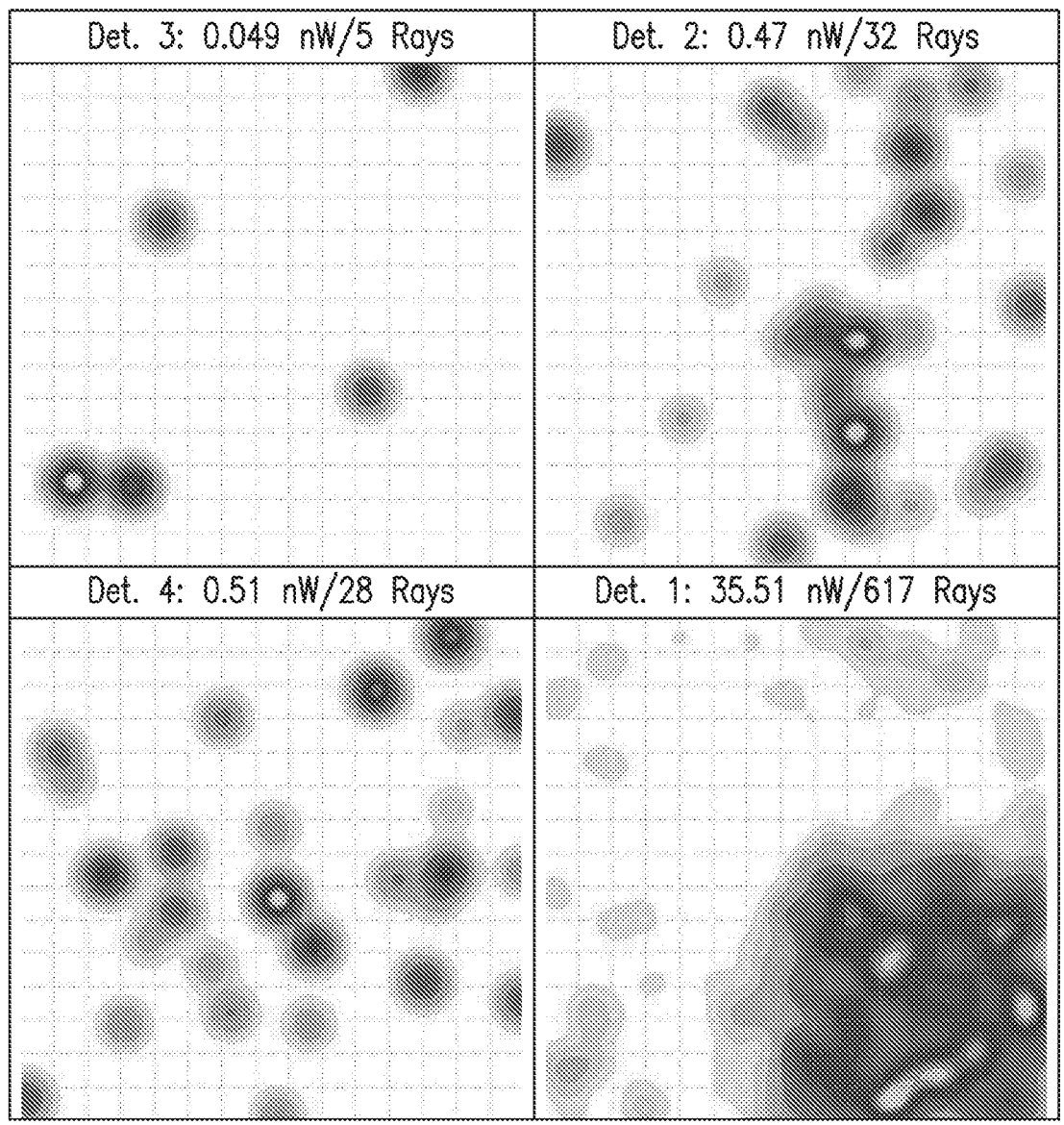
FIG. 10 provides simulated illuminance maps for a conventional planar light guide.
Figure 11:
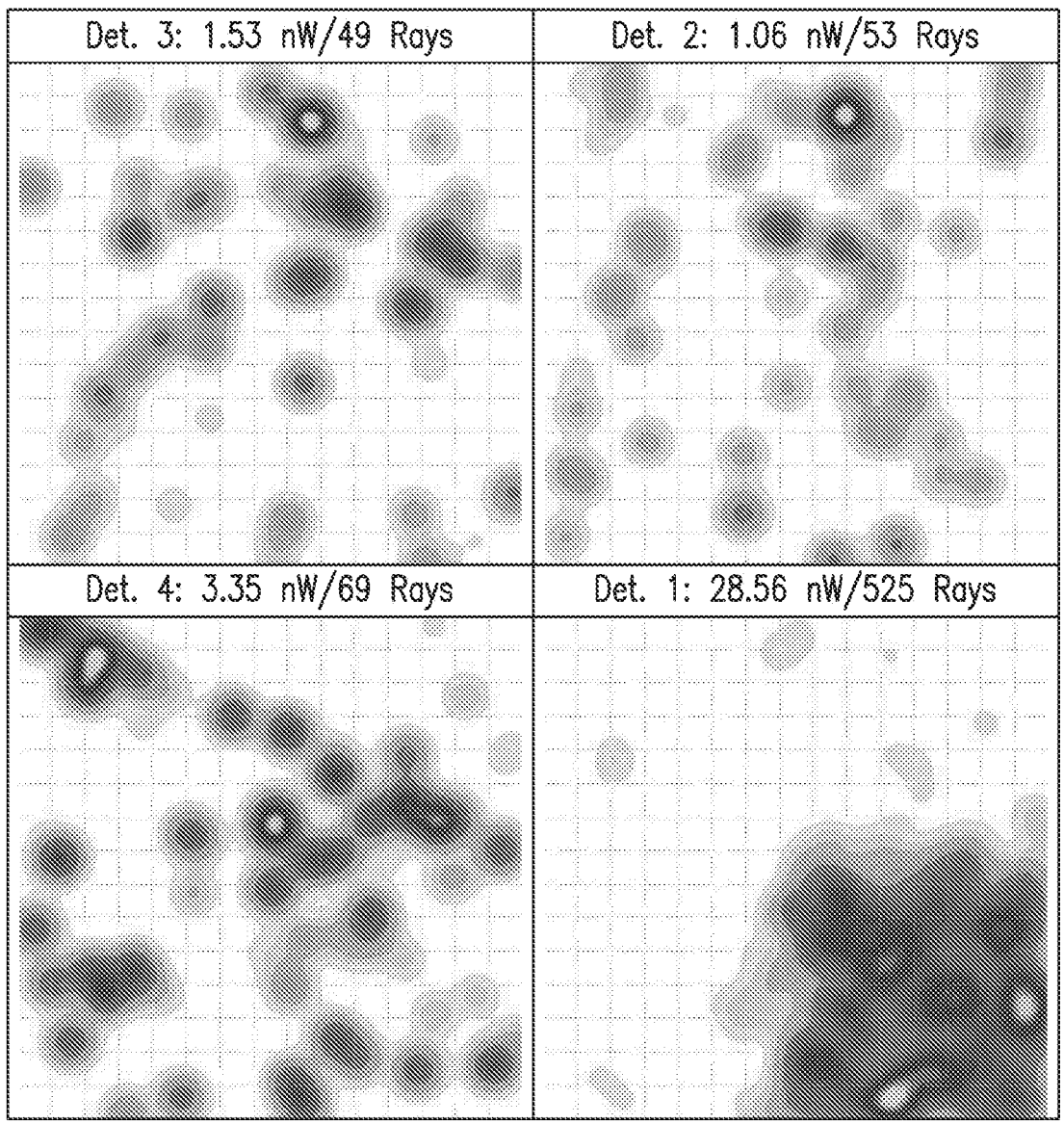
FIG. 11 provides simulated illuminance maps according to an embodiment of the present disclosure.

FIG. 10 provides simulated illuminance maps for a conventional planar light guide. FIG. 11 are simulated illuminance maps according to an embodiment of the present disclosure. The illuminance maps of FIGS. 10 and 11 are heatmaps of photon flux on respective SiPM pixels.

As shown in the conventional planar uniform light guide of FIG. 10, most light lands in a bottom right corner of the pixel corresponding to the scintillator where the gamma ray interaction took place. However, for DOI readout, a larger portion of the light would ideally be shared with neighboring pixels to gain more information on where exactly in the scintillator the interaction took place.

As shown in FIG. 11, using the same scintillator as in FIG. 10 but replacing the planar uniform light guide with the prismatoid light guide 100, the light sharing of the gamma ray interaction takes is greatly enhanced with adjacent SiPM pixels, as well as the SiPM pixels diagonally across from the original readout pixel.

Figure 12:
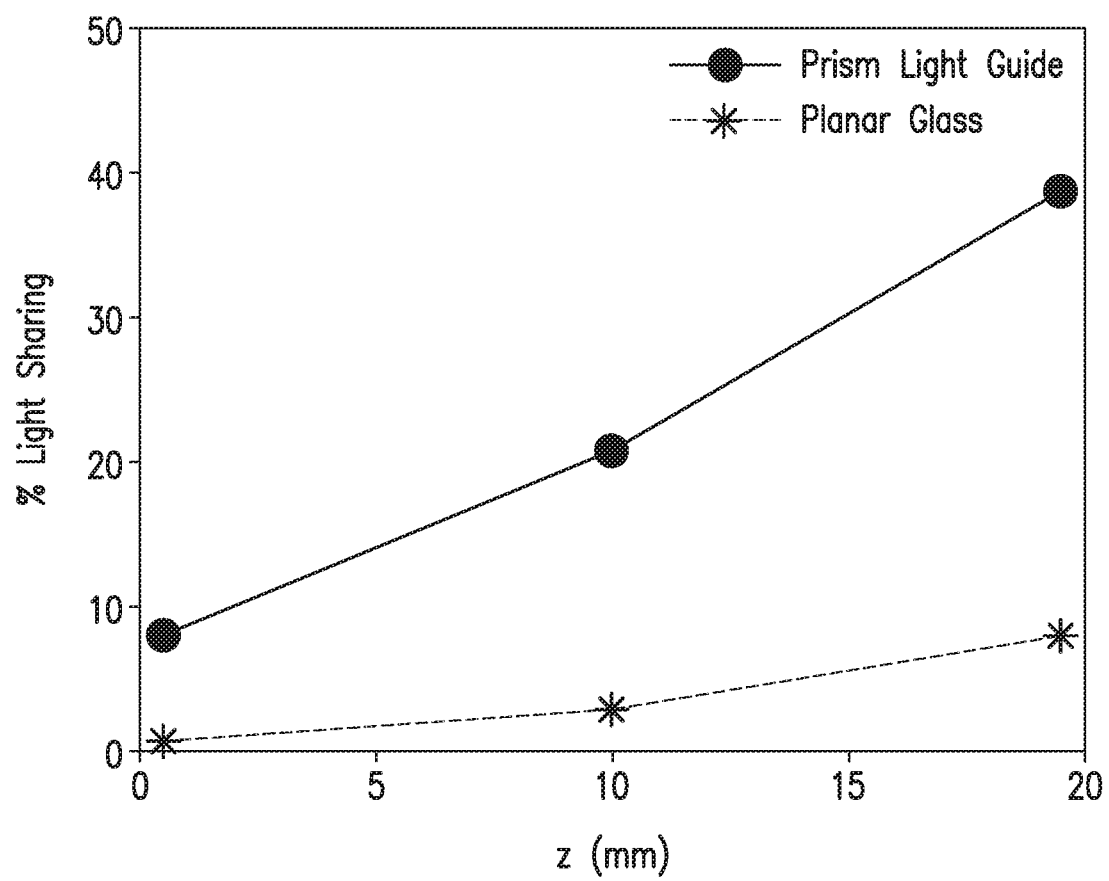
FIG. 12 is a graph of percent light-sharing across neighboring silicon photomultipliers detectors comparing the percentage light sharing of conventional planar glass with the prismatoid light guide according to an embodiment of the present disclosure.

FIG. 12 is a graph of percent light-sharing across neighboring SiPM detectors comparing percentage light sharing of conventional planar glass with the prismatoid light guide. As illustrated in FIG. 12, the prismatoid light guide 100 provides significantly improved light sharing for all interaction depths, with the improvement increasing as a function of interaction depth, illustrating enhanced DOI localization accuracy, which in turn provides improved DOI resolution and spatial resolution of PET detector systems.

A method of fabrication is provided that includes affixing the prismatoid light guide onto one end of a scintillator, which may be provided as a block of scintillator crystals, with the detector module affixed to an opposite end of the scintillator. The prismatoid 120 may be deposited on the one end of the scintillator array by sputtering. The prismatoid may also be removably attached to the one end of the scintillator. The scintillators may be polished and then de-polished along lateral faces thereof to introduce roughness and improve DOI resolution by creating differential light sharing along the lateral faces as a function of gamma ray interaction depth.

While the invention has been shown and described with reference to certain aspects thereof, it will be understood by those skilled in the art that various changes in form and details may be made therein without departing from the spirit and scope of the present invention as defined by the appended claims and equivalents thereof. No recitation of any claim set forth below is to be construed as a means plus function element without express use of "means for" or "step for."

What is claimed is:

1. A device for detecting sub-atomic particles, the device comprising:
    first scintillator;
    a second scintillator;
    a third scintillator;
    a fourth scintillator;
    at least one detector provided on a first end of the first scintillator; and
    a prismatoid provided on a second end of each of the first scintillator, the second scintillator, the third scintillator and the fourth scintillator,
    wherein the prismatoid is configured to redirect light between a first pair of adjacent scintillators of the plurality of scintillators, the first pair of adjacent scintillators including the first scintillator and the second scintillator.

2. The device of claim 1, wherein the prismatoid comprises at least one reflective surface for redirecting travel of at least one sub-atomic particle emitted from at least one of the first scintillator or the second scintillator.

3. The device of claim 2, wherein the first scintillator is scintillator, and wherein the travel of the at least one sub-atomic particle is redirected from the first scintillator toward the second scintillator.

4. The device of claim 1, wherein the prismatoid is substantially shaped as at least one of at least one prism, at least one antiprism, at least one frustum, at least one triangle, at least one cupola, at least one parallelepiped, at least one wedge, at least one pyramid; at least one truncated pyramid, or at least one portion of a sphere.

5. The device of claim 1, wherein a second pair of adjacent scintillators includes the third scintillator and the fourth scintillator,
    wherein the first scintillator of the first pair of adjacent scintillators is adjacent to a first third scintillator of the second pair of adjacent scintillators, and
    wherein the first scintillator shares a first detector of the at least one detector with the third scintillator of the second pair of adjacent scintillators.

6. The device of claim 5, wherein the second scintillator of the first pair of adjacent scintillators is adjacent to the fourth scintillator of the second pair of adjacent scintillators, and
    wherein the second scintillator of the first pair of adjacent scintillators shares a second detector of the at least one detector with the fourth scintillator of the second pair of adjacent scintillators.

7. The device of claim 6, wherein the prismatoid is configured to redirect light from the first scintillator of the first pair of adjacent scintillators to at least one of the second scintillator of the first pair of adjacent scintillators, the third scintillator of the second pair of adjacent scintillators, or the fourth scintillator of the second pair of adjacent scintillators.

8. The device of claim 1, wherein each of the first and second scintillators comprises:
    a first interior side; and
    a second interior side substantially parallel with the first interior side.

9. The device of claim 8, wherein the first interior side and the second interior side of the first scintillator or the second scintillator are configured to reflect light therebetween, for transmitting substantially all of the light from the prismatoid to the at least one detector.

10. The device of claim 1, wherein the at least one detector comprises at least one pixilated sensor.

11. The device of claim 10, further comprising at least one processor configured to communicate with the at least one pixilated sensor to perform positron emission tomography (PET) by sensing at least one photon.

12. A prismatoid comprising:
    a transparent surface adjacent to a first pair of adjacent scintillators including a first scintillator and a second scintillator, and a second pair of adjacent scintillators including a third scintillator, and a fourth scintillator; and
    a reflective surface configured to redirect travel of at least one photon emitted from the first scintillator of the first pair of adjacent scintillators through the transparent surface,
    wherein the travel of the at least one photon is redirected from the first scintillator of the first pair of adjacent scintillators toward the second scintillator of the first pair of adjacent scintillators.

13. The prismatoid of claim 12, wherein at least one detector is provided on an end of the first pair of adjacent scintillators, opposite the reflective surface, and wherein the first scintillator of the first pair of adjacent scintillators shares a first detector of the at least one detector with the third scintillator of the second pair of adjacent scintillators.

14. The prismatoid of claim 13, wherein the second scintillator of the first pair of adjacent scintillators is adjacent to the fourth scintillator of the second pair of adjacent scintillators, and
wherein the second scintillator of the first pair of adjacent scintillators shares a second detector of the at least one detector with the fourth scintillator of the second pair of adjacent scintillators.

15. The prismatoid of claim 12, wherein the prismatoid is configured to redirect light from the first scintillator of the first pair of adjacent scintillators to at least one of the second scintillator of the first pair of adjacent scintillators, the third scintillator of the second pair of adjacent scintillators, and the fourth scintillator of the second pair of adjacent scintillators.

16. The prismatoid of claim 15, wherein each of the first and second scintillators comprises:
a first interior side; and
a second interior side substantially parallel with the first interior side, and
wherein the first interior side and the second interior side of the first scintillator or the second scintillator are configured to reflect light therebetween, for transmitting substantially all of the light from the prismatoid to at least one detector.

17. The prismatoid of claim 12, wherein the prismatoid is substantially shaped as at least one of at least one prism, at least one antiprism, at least one frustum, at least one triangle, at least one cupola, at least one parallelepiped, at least one wedge, at least one pyramid, at least one truncated pyramid, or at least one portion of a sphere.

18. A system for non-invasive medical imaging, the system comprising:
at least one prismatoid;
at least one detector; and
a scintillator array comprising a first pair of adjacent scintillators including a first scintillator and a second scintillator, and a second pair of adjacent scintillators including a third scintillator, and a fourth scintillator,
wherein the at least one prismatoid is configured to redirect light between the first or second pair of adjacent scintillators of the scintillator array,
wherein the at least one detector is provided on an end of the scintillator array opposite the at least one prismatoid, and
wherein the at least one prismatoid is substantially shaped as at least one of at least one prism, at least one antiprism, at least one frustum, at least one triangle, at least one cupola, at least one parallelepiped, at least one wedge, at least one pyramid, at least one truncated pyramid, or at least one portion of a sphere.

19. The system of claim 18, further comprising a processor configured to perform positron emission tomography (PET) with a single-sided depth-of-interaction (DOI) readout.

20. The system of claim 19, wherein the scintillator array, the at least one prismatoid, and the at least one detector are asymmetrically aligned, and
wherein a first detector of the at least one detector abuts a second detector of the at least one detector, to extend an area for performing the PET.

* * * * *